United States Patent
Sun (10) Patent No.: US 11,027,271 B2
(45) Date of Patent: Jun. 8, 2021

(54) METHODS FOR PRODUCING MULTIFUNCTIONAL CATALYSTS FOR UPGRADING PYROLYSIS OIL

(71) Applicant: Saudi Arabian Oil Company, Dhahran (SA)

(72) Inventor: Miao Sun, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 0 days.

(21) Appl. No.: 16/916,234

(22) Filed: Jun. 30, 2020

(65) Prior Publication Data

US 2021/0001321 A1    Jan. 7, 2021

Related U.S. Application Data

(62) Division of application No. 16/502,633, filed on Jul. 3, 2019.

(51) Int. Cl.

| | |
|---|---|
| *B01J 29/06* | (2006.01) |
| *B01J 37/08* | (2006.01) |
| *B01J 27/19* | (2006.01) |
| *B01J 27/24* | (2006.01) |
| *B01J 29/04* | (2006.01) |
| *B01J 29/076* | (2006.01) |
| *B01J 29/70* | (2006.01) |
| *B01J 29/78* | (2006.01) |
| *B01J 35/00* | (2006.01) |
| *B01J 35/10* | (2006.01) |
| *B01J 37/02* | (2006.01) |
| *C10G 1/08* | (2006.01) |
| *C10G 35/06* | (2006.01) |
| *C07C 4/06* | (2006.01) |
| *C07C 4/26* | (2006.01) |
| *C10G 11/05* | (2006.01) |
| *C10G 65/12* | (2006.01) |

(Continued)

(52) U.S. Cl.

CPC ............. *B01J 37/082* (2013.01); *B01J 27/19* (2013.01); *B01J 27/24* (2013.01); *B01J 29/045* (2013.01); *B01J 29/061* (2013.01); *B01J 29/076* (2013.01); *B01J 29/7007* (2013.01); *B01J 29/7815* (2013.01); *B01J 35/0006* (2013.01); *B01J 35/1019* (2013.01); *B01J 35/1057* (2013.01); *B01J 35/1085* (2013.01); *B01J 37/0201* (2013.01); *B01J 37/0207* (2013.01); *C07C 4/06* (2013.01); *C07C 4/26* (2013.01); *C10G 1/086* (2013.01); *C10G 11/05* (2013.01); *C10G 35/065* (2013.01); *C10G 65/12* (2013.01); *C10G 65/14* (2013.01); *C10G 65/18* (2013.01); *C10G 67/00* (2013.01); *C10G 69/04* (2013.01); *C10G 69/06* (2013.01); *C10G 69/14* (2013.01); *B01J 2229/186* (2013.01); *B01J 2229/22* (2013.01); *B01J 2229/32* (2013.01); *B01J 2229/38* (2013.01); *C07C 2529/70* (2013.01); *C07C 2529/78* (2013.01); *C10G 2300/1033* (2013.01); *C10G 2300/4006* (2013.01); *C10G 2300/4012* (2013.01); *C10G 2300/708* (2013.01); *C10G 2400/30* (2013.01)

(58) Field of Classification Search

CPC ...... B01J 29/045; B01J 29/061; B01J 29/076; B01J 29/7815; B01J 29/7007; B01J 35/0006; B01J 35/1085; B01J 35/1057; B01J 35/1019; B01J 37/0201; B01J 37/0207; B01J 2229/186; B01J 2229/22; B01J 2229/32; B01J 2229/38; C07C 2529/70; C07C 2529/78; C10G 2400/30; C10G 2300/1033; C10G 2300/4006; C10G 2300/4012; C10G 35/065; C10G 1/086

USPC .......................................... 502/60, 73, 85, 86

See application file for complete search history.

(56) References Cited

U.S. PATENT DOCUMENTS

| | | |
|---|---|---|
| 6,531,051 B1 | 3/2003 | Kasztelan et al. |
| 9,217,114 B2 | 12/2015 | Cortright et al. |
| 9,321,973 B2 | 4/2016 | Marchand et al. |
| 10,118,163 B1 | 11/2018 | Zhang |

(Continued)

FOREIGN PATENT DOCUMENTS

| | | |
|---|---|---|
| CN | 104355995 A | 2/2015 |
| CN | 106622354 A | 5/2017 |

(Continued)

OTHER PUBLICATIONS

Nikulshin, et al., "CoMo/Al2O3 catalysts prepared on the basis of Co2Mo10-heteropolyacid and cobalt citrate: Effect of Co/Mo ratio", Fuel, vol. 100, 2012, pp. 24-33.*

(Continued)

*Primary Examiner* — Elizabeth D Wood (74) *Attorney, Agent, or Firm* — Dinsmore & Shohl LLP (57) ABSTRACT

A method of making a multifunctional catalyst for upgrading pyrolysis oil includes contacting a zeolite support with a solution including at least a first metal catalyst precursor and a second metal catalyst precursor, the first metal catalyst precursor, the second metal catalyst precursor, or both, including a heteropolyacid. Contacting the zeolite support with the solution deposits or adsorbs the first metal catalyst precursor and the second catalyst precursor onto outer surfaces and pore surfaces of the zeolite support to produce a multifunctional catalyst precursor. The method further includes removing excess solution from the multifunctional catalyst precursor and calcining the multifunctional catalyst precursor to produce the multifunctional catalyst comprising at least a first metal catalyst and a second metal catalyst deposited on the outer surfaces and pore surfaces of the zeolite support.

15 Claims, 2 Drawing Sheets

(51) Int. Cl.
    *C10G 65/14* (2006.01)
    *C10G 65/18* (2006.01)
    *C10G 67/00* (2006.01)
    *C10G 69/04* (2006.01)
    *C10G 69/06* (2006.01)
    *C10G 69/14* (2006.01)

(56) References Cited

U.S. PATENT DOCUMENTS

| | | | |
|---|---|---|---|
| 2005/0070423 | A1 | 3/2005 | Kishan et al. |
| 2009/0171123 | A1 | 7/2009 | Glaser et al. |
| 2009/0314683 | A1 | 12/2009 | Matsushita |
| 2012/0238792 | A1 | 9/2012 | Watson et al. |
| 2013/0143972 | A1 | 6/2013 | Townsend et al. |
| 2013/0164205 | A1 | 6/2013 | Putluru et al. |
| 2013/0178664 | A1 | 7/2013 | Zhou et al. |
| 2013/0245338 | A1 | 9/2013 | Weiner et al. |
| 2014/0021096 | A1 | 1/2014 | Chaumonnot et al. |
| 2014/0027346 | A1 | 1/2014 | Chaumonnot et al. |
| 2015/0231615 | A1 | 8/2015 | Bonduelle et al. |
| 2015/0274620 | A1 | 10/2015 | Zong et al. |
| 2017/0001180 | A1 | 1/2017 | Ravishankar et al. |
| 2017/0100710 | A1 | 4/2017 | Kim et al. |
| 2018/0142159 | A1 | 5/2018 | Kumar et al. |
| 2018/0290131 | A1 | 10/2018 | Carrette |
| 2018/0333708 | A1 | 11/2018 | Ding et al. |
| 2019/0134616 | A1 | 5/2019 | Jae et al. |

FOREIGN PATENT DOCUMENTS

| | | |
|---|---|---|
| FR | 3075663 A1 | 6/2019 |
| WO | 2012085358 A1 | 6/2012 |
| WO | 2017207976 A1 | 12/2017 |

OTHER PUBLICATIONS

Guerzoni et al. "Catalytic Cracking of a Hydrocarbon Mixture on Combinations of HY and HZSM-5 Zeolites" Chemistry Department, Journal of Catalysis 139, 289-303 (1993), 15 pgs.
Hanif et al. "Supported solid and heteropoly acid catalysts for production of biodiesel" Catalysis Reviews (2017) vol. 59, No. 2, 165-188, 24 pgs.
Jimenez-Cruz et al. "Molecular size evaluation of linear and branched paraffins from the gasoline pool by DFT quantum chemical calculations" Science Direct, Fuel 83 (2004) 2183-2188, 7 pgs.
Kim et al. "Novel Ni2P/zeolite catalysts for naphthalene hydrocracking to BTX" Catalysis Communications 45 (2014) 133-138, 6 pgs.
Kim et al. "Morphology effect of b-zeolite supports for Ni2P catalysts on the hydrocracking of polycyclic aromatic hydrocarbons to benzene, toluene, and xylene" Journal of Catalysis 351 (2017) 67-78, 12 pgs.
Lapinas et al. "Catalytic Hydrogenation and Hydrocracking of Fluorene: Reaction Pathways, Kinetics, and Mechanisms" Ind. Eng. Chem. Res. 1991, 30, 42-50, 9 pgs.
Leite et al. "Hydrocracking of phenanthrene over bifunctional Pt catalysts" Catalysis Today 65 (2001) 241-247, 7 pgs.
Lemberton et al. "Catalytic hydroconversion of simulated coal tars" Applied Catalysis A: General, 79 (1991) 115-126, 12 pgs.
Matsui et al. "Explanation of Product Distribution of Hydrocracking Reaction of Aromatic Hydrocarbons with Nickel-Loaded Zeolites Based on CAMD Study on Interaction between Zeolites and Substrates" Energy & Fuels (1995) 9, 435-438, 4 pgs.
Okuhara et al. "Catalytic Chemistry of Heteropoly Compounds" Advances in Catalysis, Adv Cata vol. 41 (1996) 113, 140 pgs.
Park et al. "Mild hydrocracking of 1-methyl naphthalene (1-MN) over alumina modified zeolite" Journal of Industrial and Engineering Chemistry 19 (2013) 627-632, 6 pgs.
Tailleur et al. The effect of aromatics on paraffin mild hydrocracking reactions (WNiPd/CeY—Al2O3), Fuel Processing Technology 89 (2008) 808-818, 11 pgs.
Upare et al. "Cobalt promoted Mo/beta zeolite for selective hydrocracking of tetralin and pyrolysis fuel oil into monocyclic aromatic hydrocarbons" Journal of Industrial and Engineering Chemistry 35 (2016) 99-107, 9 pgs.
Upare et al. "Selective hydrocracking of pyrolysis fuel oil into benzene, toluene and xylene over CoMo/beta zeolite catalyst" Journal of Industrial and Engineering Chemistry 46 (2017) 356-363, 8 pgs.
Park et al. "Hydro-conversion of 1-methyl naphthalene into (alkyl)benzenes over alumina-coated USY zeolite-supported NiMoS catalysts" Fuel 90 (2011) 182-189, 8 pgs.
Office Action dated Jan. 6, 2020 pertaining to U.S. Appl. No. 16/502,633, filed Jul. 3, 2019, 19 pgs.
Wang, et al., "Performance Evaluation of "Ship-in-the-Bottle" Type Heteropoly Acid Encaged Y-Type Zeolite as Catalyst for Oxidative Desulfurization", collect. czech. commun. 2011, vol. 76, No. 12, pp. 1595-1605.
Notice of Allowance dated Mar. 2, 2020 pertaining to U.S. Appl. No. 16/502,601, filed Jul. 3, 2019.
Notice of Allowance dated Mar. 11, 2020 pertaining to U.S. Appl. No. 16/502,633, filed Jul. 3, 2019.
Pasoni et al., "Heterogenization of H6PMo9V3O40 and palladium acetate in VPI-5 and MCM-41 and their use in the catalytic oxidation of benzene to phenol", Journal of Molecular Catalyst A: Chemical 134 (1998), pp. 229-235.
Technical Data Sheet, ACS Material Al-MCM-41, www.acsmaterial.com, no date available.
Kumar et al., "MCM-41, MCM-48 and related mesoporous adsorbents: their synthesis and characterization", Colloids and Surfaces A: Physicochemical and Engineering Aspects 187-188 (2001), pp. 109-116.
Office Action dated Dec. 23, 2019 pertaining to U.S. Appl. No. 16/502,601, filed Jul. 3, 2019, 16 pgs.
International Search Report and Written Opinion dated Apr. 14, 2020 pertaining to International application No. PCT/US2019/068539 filed Dec. 26, 2019.
Notice of Allowance and Fee(s) Due dated Apr. 16, 2020 pertaining to U.S. Appl. No. 16/807,980, filed Mar. 3, 2020, 15 pgs.
Notice of Allowance and Fee(s) Due dated Apr. 16, 2020 pertaining to U.S. Appl. No. 16/807,433, filed Mar. 3, 2020, 15 pgs.
Office Action dated May 11, 2020 pertaining to U.S. Appl. No. 16/807,451, filed Mar. 3, 2020, 26 pgs.
Office Action dated May 8, 2020 pertaining to U.S. Appl. No. 16/807,971, filed Mar. 3, 2020, 21 pgs.
Office Action dated May 20, 2020 pertaining to U.S. Appl. No. 16/502,633, filed Jul. 3, 2029, 12 pgs.
Martinez-Franco et al., "Hiigh-silica nanocrystalline Beta zeolites: efficient synthesis and catalytic application", Chem. Sci., 2016, 7, pp. 102-108.
International Search Report and Written Opinion dated May 27, 2020 pertaining to International application No. PCT/US2020/019620 filed Feb. 25, 2020, 15 pgs.
Notice of Allowance and Fee(s) Due dated Jul. 16, 2020 pertaining to U.S. Appl. No. 16/807,971, filed Mar. 3, 2020, 16 pgs.
Office Action dated Jul. 10, 2020 pertaining to U.S. Appl. No. 16/502,601, filed Jul. 3, 2019, 8 pgs.
U.S. Notice of Allowance and Fee(s) due dated Aug. 19, 2020 pertaining to U.S. Appl. No. 16/807,451, filed Mar. 3, 2020, 20 pgs.
Office Action dated Nov. 9, 2020 pertaining to U.S. Appl. No. 16/502,633, filed Jul. 3, 2019, 16 pgs.
Notice of Allowance and Fee(s) Due dated Nov. 12, 2020 pertaining to U.S. Appl. No. 16/502,601, filed Jul. 3, 2019, 16 pgs.
Office Action dated Nov. 19, 2020 pertaining to U.S. Appl. No. 16/909,114, filed Jun. 23, 2020, 24 pgs.
Office Action dated Feb. 10, 2020 pertaining to U.S. Appl. No. 16/502,633, filed Jul. 3, 2019, 12 pgs.
Kondoh et al., "Catalytic cracking of heavy oil over TiO2-ZrO2 catalysts under superheated steam conditions", Fuel, vol. 167, pp. 268-294, 2016.
Kondoh et al., "Effects of H2O Addition on Oil Sand Bitumen Cracking Using a CeO2-ZrO2-Al2O3-FeOx Catalyst", Energy Fuels, vol. 30, pp. 10358-10364, 2016.

(56) References Cited

OTHER PUBLICATIONS

Kondoh et al., "Upgrading of oil sand bitumen over an iron oxide catalyst using sub- and super-critical water", Fuel Processing Technology, vol. 145, pp. 96-101, 2016.

* cited by examiner

METHODS FOR PRODUCING MULTIFUNCTIONAL CATALYSTS FOR UPGRADING PYROLYSIS OIL

CROSS-REFERENCE TO RELATED APPLICATION

This application is a divisional application of U.S. patent application Ser. No. 16/502,633 filed Jul. 3, 2019, the entire disclosure of which is incorporated by reference in the present disclosure.

TECHNICAL FIELD

The present specification generally relates to multifunctional catalysts and methods for producing the multifunctional catalysts for upgrading pyrolysis oil.

BACKGROUND

Crude oil can be converted to valuable chemical intermediates and products through one or more hydrotreating processes. The hydrotreating processes can include steam cracking, in which larger hydrocarbons in the crude oil are cracked to form smaller hydrocarbons. Steam cracking units produce a bottom stream, which is referred to as pyrolysis oil. The pyrolysis oil may include an increased concentration of aromatic compounds compared to the crude oil feedstock. In many crude oil processing facilities, this pyrolysis oil is burned as fuel. However, the aromatic compounds in the pyrolysis oil can be converted to valuable chemical intermediates and building blocks. For example, aromatic compounds from the pyrolysis oil can be converted into xylenes, which can be initial building blocks for producing terephthalic acid, which can then be used to produce polyesters. The aromatic compounds in the pyrolysis oil can be used to produce many other valuable aromatic intermediates. The market demand for these valuable aromatic intermediates continues to grow.

SUMMARY

Accordingly, ongoing needs exist for improved multifunctional catalysts for upgrading pyrolysis oils. Pyrolysis oils from steam cracking processes can be upgraded to produce valuable aromatic intermediates by contacting the pyrolysis oil with a catalyst operable to convert multi-ring aromatics in the pyrolysis oil to one or more C6-C8 aromatic compounds, which can include benzene, toluene, ethylbenzene, and xylenes, other aromatic compounds, or combinations of these. Existing catalysts operable to upgrade pyrolysis oil can include multi-metal hydrocracking catalysts that have 2 or more metals supported on catalyst support. These multi-metal hydrocracking catalysts are typically prepared from conventional metal precursors, such as metallate hydrates, metal nitrates, and other conventional metal precursors.

With these multi-metal hydrocracking catalysts prepared from conventional metal precursors, large aromatic compounds (greater than 8 carbon atoms) can be converted to C6-C8 aromatic compounds at reaction temperatures in a range of 380 degrees Celsius (° C.) to 400° C. and pressures of from 6 megapascals (MPa) to 8 MPa. Maintaining the pressure in a range of 6 MPa to 8 MPa may require a greater pressure resistance of the facility and may consume a greater amount of energy compared to lesser pressure systems. In other words, the use of existing multi-metal hydrocracking catalysts to upgrade pyrolysis oil requires expensive equipment rated for greater operating pressures and can consume greater amounts of energy to maintain the pressure above 6 MPa. Reducing the pressure below 6 MPa can substantially reduce the yield of C6-C8 aromatics when upgrading using these existing multi-metal hydrocracking catalysts prepared from conventional metal catalyst precursors.

The present disclosure is directed to multifunctional catalysts for upgrading pyrolysis oil and prepared using a heteropolyacid for at least one of the metal precursors, methods of making the multifunctional catalyst, and methods of upgrading pyrolysis oil using the multifunctional catalyst. The multifunctional catalyst of the present disclosure may produce greater yields of C6-C8 aromatic compounds from upgrading pyrolysis oil at reduced reaction pressures compared to upgrading pyrolysis oil using existing multi-metal hydrocracking catalysts. The multifunctional catalyst of the present disclosure can be prepared by contacting a zeolite support with a solution containing a first metal catalyst precursor and a second metal catalyst precursor, where at least one of the first or second metal catalyst precursor is a heteropolyacid. The heteropolyacid is a compound that includes at least an acidic hydrogen, a transition metal, at least one heteroatom, and oxygen. It has been discovered that preparing the multifunctional catalyst using a heteropolyacid for at least one of the metal precursors in place of a conventional metal precursor produces a multifunctional catalyst that achieves a greater yield of C6-C8 aromatic compounds at reduced reaction pressures compared to the multi-metal hydrocracking catalysts that are currently used to upgrade pyrolysis oil. The improved yield and reduced operating pressure may increase the efficiency and may reduce the capital and operating costs of the process for upgrading pyrolysis oil.

According to one or more aspects of the present disclosure, a method for producing a multifunctional catalyst for upgrading pyrolysis oil may include contacting a zeolite support with a solution comprising at least a first metal catalyst precursor and a second metal catalyst precursor. The first metal catalyst precursor, the second metal catalyst precursor, or both, may include a heteropolyacid, and the contacting may deposit the first metal catalyst precursor and the second catalyst precursor onto outer surfaces and pore surfaces of the zeolite support to produce a multifunctional catalyst precursor. The method may further include removing excess solution from the multifunctional catalyst precursor and calcining the multifunctional catalyst precursor to produce the multifunctional catalyst comprising at least a first metal catalyst and a second metal catalyst deposited on the outer surfaces and pore surfaces of the zeolite support. In aspects of the present disclosure, a multifunctional catalyst for upgrading pyrolysis oil may be a multifunctional catalyst made by the methods of the present disclosure.

According to one or more other aspects of the present disclosure, a method for upgrading pyrolysis oil may include contacting the pyrolysis oil with a multifunctional catalyst at mild reaction conditions comprising reaction temperatures of less than 500 degrees Celsius (° C.) and pressures less than 6 megapascals (MPa). The pyrolysis oil may include multi-ring aromatic compounds. The multifunctional catalyst may be produced by a process comprising contacting a zeolite support with a solution comprising at least a first metal catalyst precursor and a second metal catalyst precursor, the first metal catalyst precursor, the second metal catalyst precursor, or both, comprising a heteropolyacid, where the contacting causes the first metal catalyst precursor and the second catalyst precursor to deposit onto outer surfaces and pore surfaces of the zeolite support to produce a multifunctional catalyst precursor. The process for producing the multifunctional catalyst may further include removing excess solution from the multifunctional catalyst precursor and calcining the multifunctional catalyst precursor to produce the multifunctional catalyst. The multifunctional catalyst may include at least a first metal catalyst and a second metal catalyst supported on the zeolite support. Contact of the pyrolysis oil with the multifunctional catalyst at the reaction conditions may convert at least a portion of the multi-ring aromatic compounds in the pyrolysis oil to one or more C6-C8 aromatic compounds.

Additional features and advantages of the described embodiments will be set forth in the detailed description, which follows, and in part will be readily apparent to those skilled in the art from that description or recognized by practicing the described embodiments, including the detailed description, which follows, the claims, as well as the appended drawings.

BRIEF DESCRIPTION OF THE DRAWINGS

The following detailed description of specific embodiments of the present disclosure can be best understood when read in conjunction with the following drawings, in which like structure is indicated with like reference numerals and in which.

Figure 1:
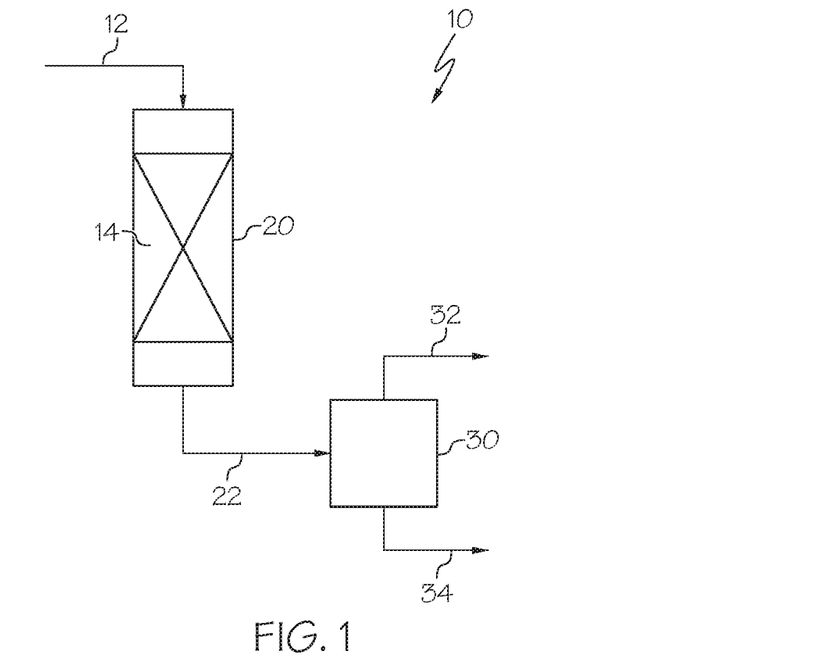
FIG. 1 schematically depicts a reactor system for upgrading pyrolysis oil, according to one or more embodiments described in this disclosure.
Figure 3:
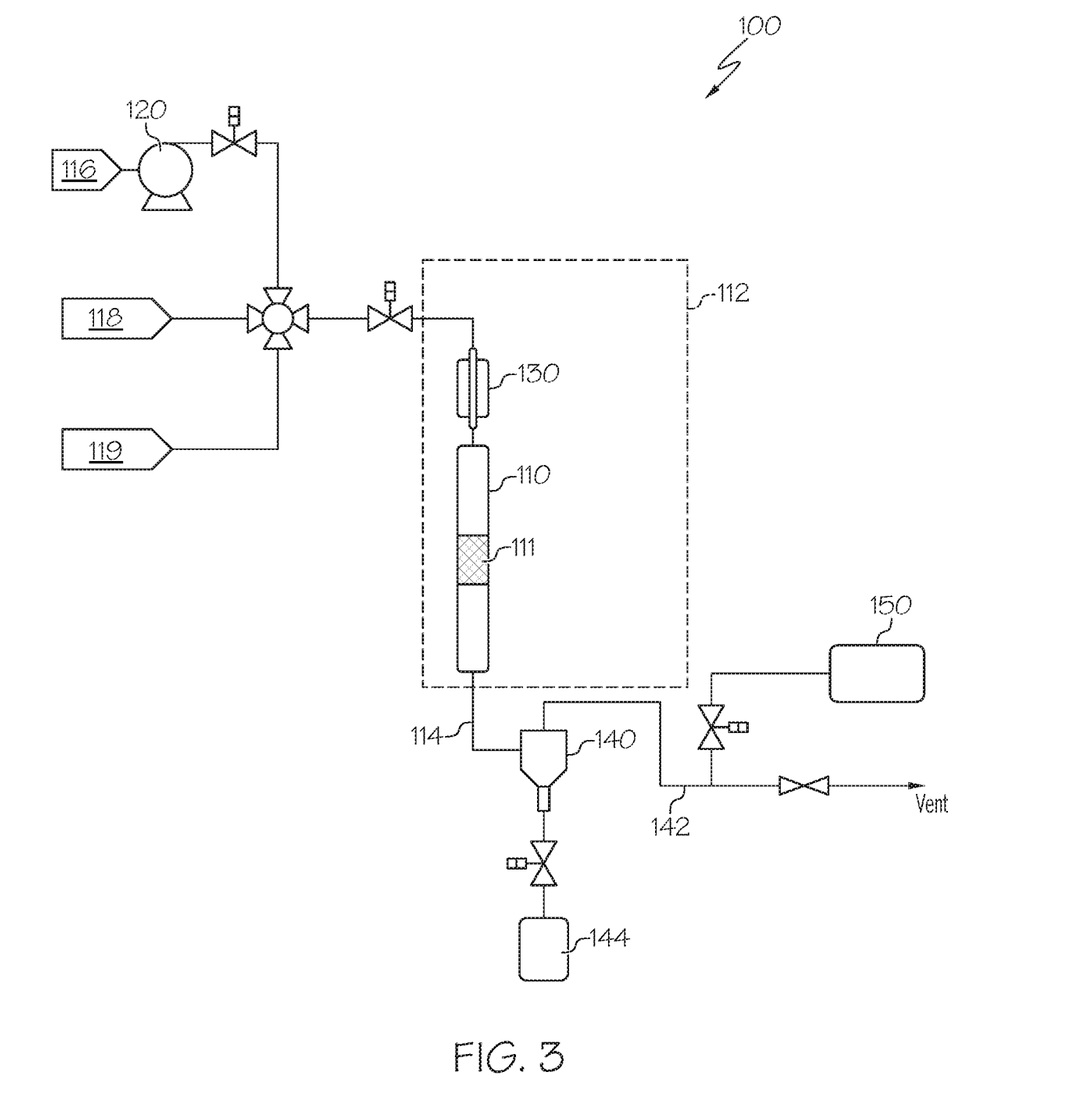
FIG. 3 schematically depicts a reactor system for upgrading a model pyrolysis oil in the Examples, according to one or more embodiments described in this disclosure.

For the purposes of describing the simplified schematic illustrations and descriptions of FIGS. 1 and 3, the numerous valves, temperature sensors, flow meters, pressure regulators, electronic controllers, pumps, and the like that may be employed and well known to those of ordinary skill in the art of certain chemical processing operations are not included. Further, accompanying components that are often included in typical chemical processing operations, such as valves, pipes, pumps, agitators, heat exchangers, instrumentation, internal vessel structures, or other subsystems, may not be depicted. Though not depicted, it should be understood that these components are within the spirit and scope of the present embodiments disclosed. However, operational components, such as those described in the present disclosure, may be added to the embodiments described in this disclosure.

Arrows in the drawings refer to process streams. However, the arrows may equivalently refer to transfer lines, which may serve to transfer process streams between two or more system components. Additionally, arrows that connect to system components may define inlets or outlets in each given system component. The arrow direction corresponds generally with the major direction of movement of the materials of the stream contained within the physical transfer line signified by the arrow. Furthermore, arrows that do not connect two or more system components may signify a product stream which exits the depicted system or a system inlet stream which enters the depicted system. Product streams may be further processed in accompanying chemical processing systems or may be commercialized as end products.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that two or more process streams are "mixed" or "combined" when two or more lines intersect in the schematic flow diagrams of FIGS. 1 and 3. Mixing or combining may also include mixing by directly introducing both streams into a like system component, such as a separation unit, reactor, or other system component. For example, it should be understood that when two streams are depicted as being combined directly prior to entering a system component, the streams could equivalently be introduced into the system component separately and be mixed in the system component.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to multifunctional catalysts for upgrading pyrolysis oil. The multifunctional catalysts include a plurality of metal catalysts supported on a zeolite support. The multifunctional catalysts of the present disclosure can be prepared using a heteropolyacid for at least one of the metal catalyst precursors. The multifunctional catalysts for upgrading pyrolysis oil of the present disclosure made using heteropolyacids for the metal catalyst precursors may provide greater yield of valuable aromatic compounds, such as benzene, toluene, ethylbenzene, and xylenes, from upgrading of the pyrolysis oil. Additionally, the multifunctional catalysts for upgrading pyrolysis oil may enable the upgrading of pyrolysis oil to be conducted at lesser reaction pressures compared to existing commercially available catalysts for upgrading pyrolysis oil.

As used in this disclosure, the term "C6-C8 aromatic compounds" may refer to one or more compounds having an aromatic ring, with or without substitution, and from 6 to 8 carbon atoms. The term "BTEX" may refer to any combination of benzene, toluene, ethylbenzene, para-xylene, meta-xylene, and ortho-xylene.

As used in this disclosure, the term "xylenes," when used without a designation of the isomer, such as the prefix para, meta, or ortho, may refer to one or more of meta-xylene, ortho-xylene, para-xylene, and mixtures of these xylene isomers.

As used in this disclosure, the terms "upstream" and "downstream" refer to the relative positioning of unit operations with respect to the direction of flow of the process streams. A first unit operation of a system is considered "upstream" of a second unit operation if process streams flowing through the system encounter the first unit operation before encountering the second unit operation. Likewise, a second unit operation is considered "downstream" of the first unit operation if the process streams flowing through the system encounter the first unit operation before encountering the second unit operation.

Referring now to FIG. 1, a system 10 for upgrading pyrolysis oil 12 is schematically depicted. The system 10 for upgrading pyrolysis oil 12 may include a reactor unit 20 and a separation unit 30 downstream of the reactor unit 20. The reactor unit 20 may include one or a plurality of reactors and may be operable to contact the pyrolysis oil 12 with a catalyst in reaction zone 14 to produce an upgraded effluent 22. The catalyst may be the multifunctional catalyst of the present disclosure. The upgraded effluent 22 may be passed to the separation unit 30, which may include one or a plurality of separation processes or unit operations. The separation unit 30 may be operable to separate the upgraded effluent 22 into one or a plurality of product streams, such as a BTEX-containing stream and a greater boiling fraction 34. Although the separation unit 30 is depicted in FIG. 1 as separating the upgraded effluent 22 into the C6-C8 aromatic stream 32 and a greater boiling fraction 34, it is understood that the separation unit 30 may be operable to separate the upgraded effluent 22 into a plurality of product streams, one of which may include a C6-C8 aromatic stream 32.

Figure 2:
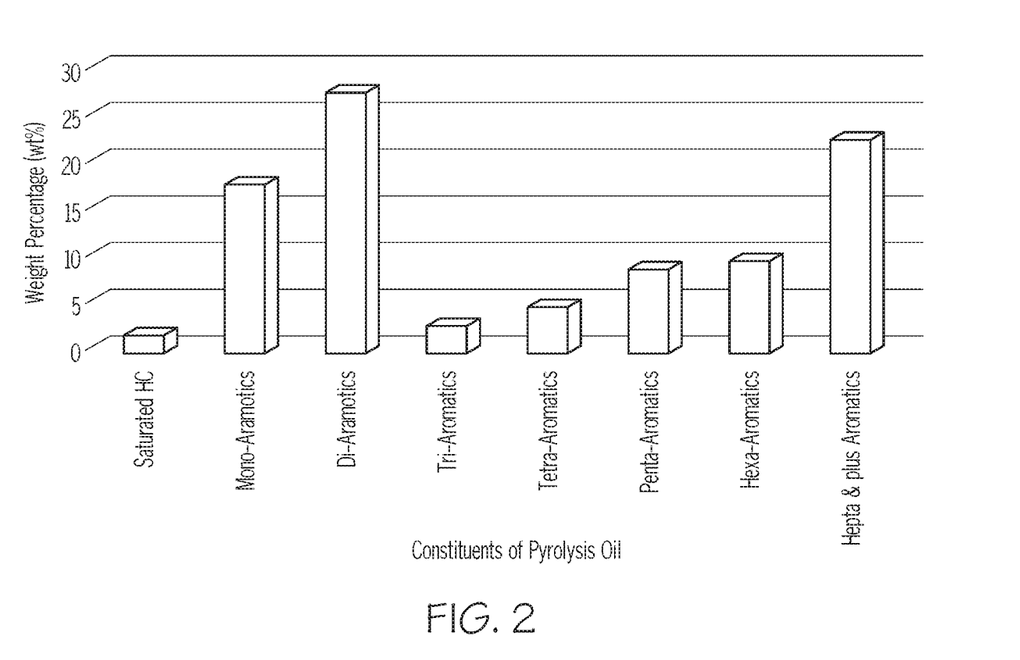
FIG. 2 graphically depicts an example composition for pyrolysis oil obtained from a steam cracking process for steam cracking crude oil, according to one or more embodiments described in this disclosure.

The pyrolysis oil 12 may be a stream from a hydrocarbon processing facility that is rich in aromatic compounds, such as multi-ring aromatic compounds. In some embodiments, the pyrolysis oil may be a bottom stream from a steam cracking process. The pyrolysis oil 12 may include mono-aromatic compounds and multi-aromatic compounds. Multi-aromatic compounds may include aromatic compounds including 2, 3, 4, 5, 6, 7, 8, or more than 8 aromatic ring structures. The pyrolysis oil 12 may also include other components, such as but not limited to saturated hydrocarbons. Referring to FIG. 2, the composition of a typical pyrolysis oil produced from steam cracking crude oil from Saudi Arabia is depicted. As shown in FIG. 2, the pyrolysis oil may include mono-aromatics, di-aromatics, tri-aromatics, tetra-aromatics, penta-aromatics, hexa-aromatics, and aromatic compounds having 7 or more aromatic rings (hepta and plus aromatics). The pyrolysis oil may include elevated concentrations of di-aromatic compounds and aromatic compounds having greater than 7 aromatic rings, as indicated by FIG. 2. In some embodiments, the pyrolysis oil that is rich in multi-aromatic compounds may include greater than or equal to 50 weight percent (wt. %) multi-aromatic compounds, such as greater than or equal to 60 wt. %, greater than or equal to 65 wt. %, greater than or equal to 70 wt. %, greater than or equal to 75 wt. %, or even greater than or equal to 80 wt. % multi-aromatic compounds based on the unit weight of the pyrolysis oil. The pyrolysis oil may also have a low concentration of sulfur and sulfur compounds. The pyrolysis oil may have a concentration of sulfur and sulfur-containing compounds of less than or equal to 500 parts per million by weight (ppmw), such as less than or equal to 400 ppmw, or even less than or equal to 300 ppmw.

The multi-aromatic compounds in the pyrolysis oil may be upgraded to C6-C8 aromatic compounds through contact with the catalyst at the reaction temperature and pressure. Converting di-aromatic and multi-aromatic compounds to C6-C8 aromatic compounds, such as benzene, toluene, ethylbenzene, and xylenes, is a complicated reaction that may include multiple synchronized and selective reactions, which may include selective hydrogenation of one aromatic ring in a compound but not all, subsequent ring opening of the saturated naphthenic ring, hydro-dealkylation, and transalkylation.

This complex sequence of synchronized reactions for upgrading pyrolysis oil may be catalyzed using a multi-metallic catalyst having at least catalytic transition metals. In conventional upgrading processes, the catalyst used to upgrade the pyrolysis oil may be a multi-metal hydrocracking catalyst. These multi-metal hydrocracking catalysts are often synthesized using conventional metal precursors, such as metallate hydrates, metal nitrates, metal carbonates, metal hydroxides, other conventional metal precursors, or combinations of these conventional metal precursors.

With these multi-metal hydrocracking catalysts made from conventional metal precursors, large aromatic compounds (greater than 8 carbon atoms) can be converted to C6-C8 aromatic compounds, such as but not limited to benzene, toluene, ethylbenzene, or xylenes (BTEX), at reaction temperatures in a range of 380° C. to 400° C. and pressures of from 6 megapascals (MPa) to 8 MPa. Maintaining the pressure in a range of 6 MPa to 8 MPa may require a greater pressure resistance of the facility and may consume a greater amount of energy compared to reactions conducted on lesser reaction pressures. In other words, the use of existing multi-metal hydrocracking catalysts to upgrade pyrolysis oil may require expensive equipment, which is rated for greater operating pressures, and can consume greater amounts of energy to maintain the pressure above 6 MPa. Additionally, the yield of C6-C8 aromatic compounds using these existing multi-metal hydrocracking catalysts is low. Reducing the pressure below 6 MPa can further reduce the yield of C6-C8 aromatic compounds when upgrading using existing multi-metal hydrocracking catalysts.

As previously discussed, the present disclosure is directed to a multifunctional catalyst for upgrading pyrolysis oil, the multifunctional catalyst being produced by utilizing one or more heteropolyacids as the metal precursors for one or more of the metal catalysts of the multifunctional catalyst. The methods of making the multifunctional catalyst for upgrading pyrolysis oil may include contacting a zeolite support with a solution comprising at least a first metal catalyst precursor and a second metal catalyst precursor, the first metal catalyst precursor, the second metal catalyst precursor, or both, comprising a heteropolyacid. Contacting the zeolite support with the solution may result in deposition or adsorption of the first metal catalyst precursor and the second catalyst precursor onto outer surfaces and pore surfaces of the zeolite support to produce a multifunctional catalyst precursor. The method may further include removing the excess solution and solvent from the multifunctional catalyst precursor and calcining the multifunctional catalyst precursor to produce the multifunctional catalyst, which includes at least a first metal catalyst and a second metal catalyst deposited on the outer surfaces and pore surfaces of the zeolite support.

The multifunctional catalysts made by the methods of the present disclosure may increase the yield of BTEX from upgrading pyrolysis oil compared to existing multi-metal hydrocracking catalysts. Additionally, as compared to existing multi-metal hydrocracking catalysts, the multifunctional catalysts made by the methods of the present disclosure may also enable upgrading of the pyrolysis oil to be conducted at the same reaction temperature and reduced reaction pressure, such as a reaction pressure less than or equal to 5 MPa. The reduced reaction pressure enabled by the multifunctional catalysts of the present disclosure may reduce the capital and operating costs of systems for upgrading pyrolysis oils.

The method of making the multi-functional catalyst may include providing a zeolite support. The zeolite support may be a nano-zeolite having an average pore size of less than or equal to 2 micrometers (μm), or even less than or equal to 1 μm. The zeolite support may have a molar ratio of silica ($SiO_2$) to alumina ($Al_2O_3$) of greater than or equal to 10, such as greater than or equal to 20, greater than or equal to 30, greater than or equal to 40, greater than or equal to 50, or greater than or equal to 60. The zeolite support may have a molar ratio of $SiO_2$ to $Al_2O_3$ of less than or equal to 70, such as less than or equal to 60, less than or equal to 50, less than or equal to 40, less than or equal to 30, or even less than or equal to 20. The zeolite support may have a molar ratio of $SiO_2$ to $Al_2O_3$ of from 10 to 70. In some embodiments, the zeolite support may have a molar ratio of $SiO_2$ to $Al_2O_3$ of from 10 to 60, from 10 to 50, from 10 to 40, from 20 to 70, from 20 to 60, from 20 to 50, from 20 to 40, from 30 to 70, from 30 to 60, from 30 to 50, from 40 to 70, from 40 to 60, from 50 to 70, or from 10 to 30. In some embodiments, the zeolite support may be a beta zeolite support. In some embodiments, the zeolite support may be a nano-beta zeolite support having an average pore size of less than or equal to 2 μm.

The methods of making the multifunctional catalyst for upgrading pyrolysis oil may be a wet impregnation method in which at least one of the metal catalyst precursors is a heteropolyacid. The methods may include contacting the zeolite support with the solution that includes at least the first metal catalyst precursor, the second metal catalyst precursor, and a solvent. The solution may also include a phosphorous-containing compound. The first metal catalyst precursor may include a first metal, and the second metal catalyst precursor may include a second metal different from the first metal. The first metal and the second metal may be transition metals, such as, but not limited to transition metals in Groups 5, 6, 7, 8, 9, and 10 of the International Union of Pure and Applied Chemistry (IUPAC) periodic table of elements. In some embodiments, the first metal of the first metal catalyst precursor may be a metal selected from cobalt, molybdenum, vanadium, or combinations of these. In some embodiments, the second metal of the second metal catalyst precursor may be a metal selected from cobalt, molybdenum, vanadium, or combinations of these, and may be different from the first metal.

The first metal catalyst precursor, the second metal catalyst precursor, or both may be a heteropolyacid. The heteropolyacid may include cobalt, molybdenum, or a combination of cobalt and molybdenum; at least one heteroatom selected from phosphorous (P), silicon (Si), arsenic (As), germanium (Ge), or combinations of these; and one or more than one acidic hydrogen. As used in this disclosure, the term "acidic hydrogen" may refer to a hydrogen atom of the heteropolyacid that may have a tendency to dissociate from the heteropolyacid in solution to form a positive ion. The heteropolyacid may also include oxygen. Heteropolyacids suitable for the first metal catalyst precursor, the second metal catalyst precursor, or both may have a Keggin structure having general formula $XM_{12}O_{40}{}^{n-}$ or a Dawson structure having the general formula $XM_{18}O_{82}{}^{n-}$, in which X is the heteroatom selected from phosphorous, silicon, arsenic, germanium, or combinations of these; M is the molybdenum and optionally one or more of cobalt, vanadium, or a combination of these; and n– is an integer indicative of the charge of the anion of the heteropolyacid. Examples of heteropolyacids may include, but are not limited to phosphormolybdic heteropolyacid ($H_3PMo_{12}O_{40}$), silicomolybdic heteropolyacid ($H_4SiMo_{12}O_{40}$), decamolybdiccobaltate heteropolyacid ($H_6[Co_2Mo_{10}O_{38}H_4]$), $H_4[PCoMo_{11}O_{40}]$, $H_4[PVMo_{11}O_{40}]$, $H_5[PV_2Mo_{10}O_{40}]$, $H_7[PV_4Mo_8O_{40}]$, $H_9[PV_6Mo_6O_{40}]$, $H_3[AsMo_{12}O_{40}]$, $H_4[AsCoMo_{11}O_{40}]$, $H_5[AsCo_2Mo_{10}O_{40}]$, $H_4[AsVMo_{11}O_{40}]$, $H_5[AsV_2Mo_{10}O_{40}]$, $H_7[AsV_4Mo_8O_{40}]$, $H_9[AsV_6Mo_6O_{40}]$, $H_5[SiCoMo_{11}O_{40}]$, $H_6[SiCo_2Mo_{10}O_{40}]$, $H_5[SiVMo_{11}O_{40}]$, $H_6[SiV_2Mo_{10}O_{40}]$, $Hio[SiV_6Mo_6O_{40}]$, $H_6[P_2Mo_{18}O_{82}]$, other heteropolyacids, salts of these heteropolyacids, or combinations of heteropolyacids. Salts of these heteropolyacids may include alkali metal salts, alkaline earth metal salts, nitrate salts, sulfate salts, or other salts of the heteropolyacid. Alkali metals may include sodium, potassium, rubidium, caesium, or combinations of these. Alkaline earth metals may include, but are not limited to magnesium, calcium, or combinations of these. In some embodiments, the heteropolyacid may include phosphormolybdic heteropolyacid having formula $H_3[PMo_{12}O_{40}]$. In some embodiments, the heteropolyacid may include decamolybdodicobaltate heteropolyacid having chemical formula $H_6[Co_2Mo_{10}O_{38}H_4]$. In some embodiments, the heteropolyacid may be silicomolybdic heterpolyacid having chemical formula $H_4[SiMo_{12}O_{40}]$. In some embodiments, the first metal catalyst precursor, the second catalyst precursor, or both may be a metal salt of a heteropolyacid, such as an alkali metal salt or alkaline metal salt of the heteropolyacid.

As previously described, the first metal catalyst precursor, the second metal catalyst precursor, or both may be a heteropolyacid. In some embodiments, the first metal catalyst precursor may include a heteropolyacid, and the second metal catalyst precursor may include a non-heteropolyacid precursor. In some embodiments, both the first metal catalyst precursor and the second metal catalyst precursor may include heteropolyacids. In some embodiments, the first metal catalyst precursor may include a first heteropolyacid, and the second metal catalyst precursor may include a second heteropolyacid that is different from the first heteropolyacid. For example, in some embodiments, the first metal catalyst precursor may include a first heteropolyacid that includes molybdenum as the metal, and the second metal catalyst precursor may include a second heteropolyacid that includes cobalt as the metal. In some embodiments, the first metal catalyst precursor and the second metal catalyst precursor may include the same heteropolyacid, and the heteropolyacid may include a first metal, a second metal that is different from the first metal, and at least one heteroatom. For example, in some embodiments, the solution may include decamolybdiccobaltate heteropolyacid having chemical formula $H_6[Co_2Mo_{10}O_{38}H_4]$, which includes both cobalt and molybdenum and may serve as both the first metal catalyst precursor and the second metal catalyst precursor.

In some embodiments, one of the first metal catalyst precursor or the second metal precursor may include a non-heteropolyacid metal catalyst precursor, such as a metallate hydrate, metal nitrate, and other non-heteropolyacid precursor. The solution may also include a phosphorous-containing compound, such as, but not limited to, phosphoric acid, phosphorous acid, or other phosphorous-containing compounds.

The first metal catalyst precursor and the second metal catalyst precursor may be dispersed or dissolved in a solvent to form the solution. The solvent may be water. The solvent may additionally include one or more organic solvents, such as but not limited to organic alcohols or other organic solvents. One or more than one of the heteropolyacids may be dehydrated prior to combining the heteropolyacid with the solvent to produce the solution. The solution may have a concentration of the first metal catalyst precursor sufficient to result in the first metal catalyst precursor being deposited on or adsorbed onto the outer surfaces and pore surfaces of the zeolite support. The solution may have greater than or equal to 1 wt. %, greater than or equal to 2 wt. %, greater than or equal to 5 wt. % or even greater than or equal to 10 wt. % first metal catalyst precursor based on the total weight of the solution before contact with the zeolite support. The solution may have less than or equal to 20 wt. %, less than or equal to 15 wt. %, or even less than or equal to 12 wt. % first metal catalyst precursor based on the total weight of the solution before contact with the zeolite support. In some embodiments, the solution may include from 1 wt. % to 20 wt. % of the first metal catalyst precursor, such as from 1 wt. % to 15 wt. %, from 1 wt. % to 10 wt. %, from 1 wt. % to 5 wt. %, from 2 wt. % to 20 wt. %, from 2 wt. % to 15 wt. %, from 2 wt. % to 10 wt. %, or from 2 wt. % to 5 wt. % first metal catalyst precursor based on the total weight of the solution before contact with the zeolite support.

The solution may have a concentration of the second metal catalyst precursor sufficient to result in the second metal catalyst precursor being deposited on or adsorbed onto the outer surfaces and pore surfaces of the zeolite support. The solution may have greater than or equal to 1 wt. %, greater than or equal to 2 wt. %, greater than or equal to 5 wt. % or even greater than or equal to 10 wt. % second metal catalyst precursor based on the total weight of the solution before contact with the zeolite support. The solution may have less than or equal to 20 wt. %, less than or equal to 15 wt. %, or even less than or equal to 12 wt. % second metal catalyst precursor based on the total weight of the solution before contact with the zeolite support. In some embodiments, the solution may include from 1 wt. % to 20 wt. % of the second metal catalyst precursor, such as from 1 wt. % to 15 wt. %, from 1 wt. % to 10 wt. %, from 1 wt. % to 5 wt. %, from 2 wt. % to 20 wt. %, from 2 wt. % to 15 wt. %, from 2 wt. % to 10 wt. %, or from 2 wt. % to 5 wt. % second metal catalyst precursor based on the total weight of the solution before contact with the zeolite support.

The solution may be prepared and the zeolite support may be contacted with the solution at ambient conditions. The solution may be mixed for a period of time prior to contacting the zeolite support with the solution. The mixture comprising the zeolite support dispersed in the solution may be mixed for a period of time long enough to provide sufficient adsorption or deposition of the first metal catalyst precursor and the second metal catalyst precursor onto the outer surfaces and pore surfaces of the zeolite support. Contacting of the zeolite support with the solution containing the first metal catalyst precursor and the second metal catalyst precursor may result in a mixture of a multifunctional catalyst precursor dispersed in the solution. The mixture may also include the remaining first metal catalyst precursor, second metal catalyst precursor, and any other constituents that are not adsorbed onto the outer surfaces and pore surfaces of the zeolite support. The multifunctional catalyst precursor may include at least the first metal catalyst precursor and the second metal catalyst precursor deposited on or adsorbed onto the outer surfaces or pore surfaces of the zeolite support.

As previously discussed, after contacting the zeolite support with the solution comprising the first metal catalyst precursor and the second metal catalyst precursor, the excess liquids, such as solution or solvent, may be removed from the mixture to produce a multifunctional catalyst precursor. Removing the liquid components may include removing the excess solution from the multifunctional catalyst precursor and drying the multifunctional catalyst precursor. Removing the excess solution from the multifunctional catalyst precursor may include subjecting the mixture to decantation, filtration, vacuum filtration, or combinations of these. In some embodiments, removing the liquids from the mixture may include vacuum filtration of the mixture at a temperature of from 25° C. to 90° C. Drying the multifunctional catalyst precursor may include maintaining the multifunctional catalyst precursor at a temperature greater than or equal to the boiling temperature of the solvent, such as at a temperature of from 90° C. to 200° C. Drying may be conducted for a drying period sufficient to remove the solvent to a level of less than 1 wt. % of the total weight of the multifunctional catalyst precursor. The drying period may be from 1 hour to 24 hours, such as from 2 hours to 12 hours. Drying may remove additional solvent from the multifunctional catalyst through evaporation of the solvent. In some embodiments, the solvent may be water, and drying may include maintaining the multifunctional catalyst precursor at a temperature of greater than or equal to 100° C. for a drying period of greater than or equal to 1 hour.

As previously discussed, the method may further include calcining the multifunctional catalyst precursor to produce the multifunctional catalyst of the present disclosure. Calcining the multifunctional catalyst precursor may be conducted after removal of the excess solution and solvent from the multifunctional catalyst precursor. The multifunctional catalyst precursor may be calcined at a temperature of from 500° C. to 600° C. and for a calcination period of from 4 hours to 6 hours to produce the multifunctional catalyst.

The methods described in this disclosure are based on wet impregnation of the first and second catalyst precursors onto the outer surfaces and pore surfaces of the zeolite support. It is understood that other methods of making the multifunctional catalyst using heteropolyacids for one or more than one of the metal catalyst precursors may also be employed. Such methods for making the multifunctional catalyst for upgrading pyrolysis oil may include, but are not limited to, co-precipitation methods, for example.

The multifunctional catalyst for upgrading pyrolysis oil produced by the methods described in this disclosure may include at least a first metal catalyst and a second metal catalyst supported on the outer surfaces and pore surfaces of a zeolite support. The first metal catalyst and the second metal catalyst may include any of the metals previous described in this disclosure for the first metal catalyst and second metal catalyst, respectively. The multifunctional catalyst may also include the heteroatom from the heteropolyacid—such as but not limited to phosphorous, silicon, arsenic, or combinations of these—supported on the outer surfaces or pore surfaces of the zeolite support. In some embodiments, the first metal catalyst may be molybdenum and the second metal catalyst may be cobalt or vanadium, where at least the molybdenum is provided by the heteropolyacid. In some embodiments, the cobalt may also be provided by the same or a different heteropolyacid from the heteropolyacid that contributes the molybdenum. In some embodiments, the multifunctional catalyst may include molybdenum, cobalt, and phosphorous deposited on the outer surfaces and pore surfaces of a nano beta zeolite support, where at least the molybdenum and the phosphorous are provided by the heteropolyacid. In some embodiments, the multifunctional catalyst may include molybdenum, cobalt, and silicon deposited on the outer surfaces and pore surfaces of a nano beta zeolite support.

The use of a heteropolyacid for at least one of the metal catalyst precursors may reduce the acidity and surface area of the multifunctional catalyst compared to commercially available catalyst for upgrading pyrolysis oil prepared using conventional metal catalyst precursors. The multifunctional catalyst for upgrading pyrolysis oil of the present disclosure made using one or more than one heteropolyacid may have an acidity less than an acidity of an existing commercially available catalyst having the same metal catalyst species but made with conventional metal catalyst precursors. The multifunctional catalyst may have an acidity less than 10,000 micromoles of ammonia per gram ($\mu$mol($NH_3$)/g), less than or equal to 7,000 $\mu$mol($NH_3$)/g, less than or equal to 5,000 $\mu$mol($NH_3$)/g, or even less than or equal to 4,000 $\mu$mol ($NH_3$)/g. In some embodiments, the multifunctional catalyst may have an acidity of from 1,000 $\mu$mol($NH_3$)/g to 5,000 $\mu$mol($NH_3$)/g.

The multifunctional catalyst for upgrading pyrolysis oil producing with one or more than one heteropolyacid for at least one of the metal catalyst precursors may have a reduced BET surface area compared to existing commercially available catalysts for upgrading pyrolysis oil produced with conventional metal catalyst precursors. As used herein, "BET surface area" refers to the average surface area of the metallic oxide particles as measured by the BET (Brunauer Emmett Teller) nitrogen absorption method according to ASTM D-6556. The multifunctional catalyst may have a BET surface area less than the BET surface area of the zeolite support before preparing the multifunctional catalyst. The multifunction catalyst may have a BET surface area of less than or equal to 400 meters squared per gram ($m^2/g$), less than or equal to 375 $m^2/g$, less than or equal to 350 $m^2/g$, or even less than or equal to 325 $m^2/g$. In some embodiments, the multifunctional catalyst may have a BET surface area of from 200 $m^2/g$ to 400 $m^2/g$, such as from 200 $m^2/g$ to 375 $m^2/g$, from 200 $m^2/g$ to 350 $m^2/g$, or from 200 $m^2/g$ to 325 $m^2/g$.

In some embodiments, the multifunctional catalyst for upgrading pyrolysis oil may be a multifunctional catalyst produced by a process that may include contacting the zeolite support with the solution comprising at least the first metal catalyst precursor and the second metal catalyst precursor. The first metal catalyst precursor, the second metal catalyst precursor, or both, may include a heteropolyacid. Contacting the zeolite support with the solution may cause the first metal catalyst precursor and the second catalyst precursor to deposit onto outer surfaces and pore surfaces of the zeolite support to produce a multifunctional catalyst precursor. The zeolite support may include any of the zeolite supports and may have any characteristics of the zeolite supports previously described in this disclosure. The solution, first metal catalyst precursor, second metal catalyst precursor, and one or more heteropolyacids may have any of the compositions, properties, or characteristics previously described in this disclosure for these. The method may further include removing the excess solution from the multifunctional catalyst precursor, and calcining the multifunctional catalyst precursor to produce the multifunctional catalyst. Each of the contacting step, removing excess solution step, and calcining step may be conducted under any of the process conditions previously described in this disclosure in relation to each of these process steps. The multifunctional catalyst produced by this method may include at least a first metal catalyst and a second metal catalyst deposited on the outer surfaces and the pore surfaces of the zeolite support. The multifunctional catalyst may have any of the compositions or properties previously described in this disclosure for the multifunctional catalyst.

The multifunctional catalyst prepared by the methods described in this disclosure may be used to upgrade pyrolysis oil to produce one or more valuable aromatic intermediates, such as but not limited to benzene, toluene, ethylbenzene, xylenes, other aromatic compounds, or combinations of these. In some embodiments, a method for upgrading pyrolysis oil may include contacting the pyrolysis oil with the multifunctional catalyst at mild reaction conditions comprising reaction temperatures of less than 500° C. and pressures less than 6 MPa. The pyrolysis oil may have any of the compositions or characteristics previously described in this disclosure for pyrolysis oil. In some embodiments, the pyrolysis oil may include multi-ring aromatic compounds. The multifunctional catalyst may be made by of the methods or processes for making the multifunctional catalyst described in this disclosure and may have any properties, compositions, or attributes described in this disclosure for the multifunctional catalyst. In some embodiments, the multifunctional catalyst may be produced by a process that includes contacting the zeolite support with the solution comprising at least the first metal catalyst precursor and the second metal catalyst precursor, the first metal catalyst precursor, the second metal catalyst precursor, or both, including a heteropolyacid. The contacting may cause the first metal catalyst precursor and the second catalyst precursor to deposit or be adsorbed onto the outer surfaces and pore surfaces of the zeolite support to produce a multifunctional catalyst precursor. The process for producing the multifunctional catalyst may include removing excess solution from the multifunctional catalyst precursor, and calcining the multifunctional catalyst precursor to produce the multifunctional catalyst. The multifunctional catalyst may include a first metal catalyst and a second metal catalyst supported on the zeolite support.

Contact of the pyrolysis oil with the multifunctional catalyst at the reaction conditions may convert at least a portion of the multi-ring aromatic compounds in the pyrolysis oil to one or more C6-C8 aromatic compounds. The at least a portion of the multi-ring aromatic compounds converted to one or more C6-C8 compounds may include at least 30%, at least 40%, at least 50%, at least 60%, at least 70%, or at least 80% of the multi-ring aromatic compounds in the pyrolysis oil. The C6-C8 aromatic compounds may include, but are not limited to, one or more of benzene, toluene, ethylbenzene, xylene, or combinations of these. In some embodiments, contacting the pyrolysis oil with the multifunctional catalyst at the reactions conditions may convert the portion of the multi-ring aromatic compounds in the pyrolysis oil to C6-C8 aromatic compounds in a single step, without conducting a subsequent chemical reaction step.

Contacting of the pyrolysis oil with the multifunctional catalyst may be conducted at a reaction temperature in a range comparable to the reaction temperatures for processes for upgrading pyrolysis oil using commercially-available catalysts prepared using conventional metal catalyst precursors. In some embodiments, the pyrolysis oil may be contacted with the multifunctional catalyst at a reaction temperature of less than or equal to 500° C., less than or equal to 450° C., or even less than or equal to 400° C. The pyrolysis oil may be contacted with the multifunctional catalyst at a reaction temperature of greater than or equal to 350° C., greater than or equal to 380° C., or even greater than or equal to 400° C. In some embodiments, pyrolysis oil may be contacted with the multifunctional catalyst at a reaction temperature of from 350° C. to 500° C., from 350° C. to 450° C., from 350° C. to 400° C., from 380° C. to 500°

C., from 380° C. to 450° C., from 380° C. to 400° C., from 400° C. to 500° C., or from 400° C. to 425° C.

Contacting of the pyrolysis oil with the multifunctional catalyst may be conducted at a reaction pressure less than the reactions pressures necessary for upgrading pyrolysis oil using the commercially-available catalysts prepared using conventional metal catalyst precursors. In some embodiments, the pyrolysis oil may be contacted with the multifunctional catalyst at a reaction pressure less than 6 MPa, less than or equal to 5 MPa, or even less than or equal to 4 MPa. In some embodiments, the pyrolysis oil may be contacted with the multifunctional catalyst at a reaction pressure greater than or equal to 0.1 MPa, greater than or equal to 1 MPa, or even greater than or equal to 2 MPa. In some embodiments, the pyrolysis oil may be contacted with the multifunctional catalyst at a reaction pressure of from 0.1 MPa to 5 MPa, from 0.1 MPa to 4 MPa, from 1 MPa to 5 MPa, from 1 MPa to 4 MPa, from 2 MPa to 5 MPa, or even from 2 MPa to 4 MPa.

In some embodiments, the method of upgrading pyrolysis oil may further include separating an upgraded pyrolysis oil from the multifunctional catalyst. Separating the upgraded pyrolysis oil from the multifunctional catalyst may be conducted using any known method or process of separating a fluid from a particulate solid.

Upgrading pyrolysis oil by contacting with the multifunctional catalyst of the present disclosure prepared using heteropolyacids may produce a greater yield of C6-C8 aromatic compounds, such as one or more than one of benzene, toluene, ethylbenzene, xylenes, or combinations of these, compared to upgrading the pyrolysis oil by contacting with commercially-available catalysts prepared using conventional metal catalyst precursors. In some embodiments, upgrading pyrolysis oil by contacting the pyrolysis oil with the multifunctional catalyst of the present disclosure prepared using heteropolyacids may produce a combined yield of C6-C8 aromatic compounds of greater than or equal to 30 wt. %, greater than or equal to 32 wt. %, or even greater than or equal to 35 wt. %, based on the total weight of the upgraded pyrolysis oil separated from the multifunctional catalyst.

EXAMPLES

The following examples illustrate the methods of the present disclosure for producing multifunctional catalysts for upgrading pyrolysis oil and the methods for upgrading pyrolysis oil using the multifunctional catalysts. The Examples are not intended to limit the scope of the present disclosure in any way, in particular with respect to specific mass flow rates, stream compositions, temperatures, pressures, time on stream, amounts of catalytic metals on the zeolite support, or other variables fixed for the purposes of conducting the experiments.

Comparative Example 1: Nano-Beta Zeolite Support

For Comparative Example 1, beta zeolite support particles with no metal compounds deposited on the outer surfaces or pore surfaces were provided as a baseline comparison. It is noted that beta zeolite by itself provides at least some activity for catalyzing cracking of hydrocarbons. The beta zeolite support of Comparative Example 1 was CP814E nano-beta zeolite obtained from Zeolyst International. The nano-beta zeolite support particles had a ratio of the molar amount of silica ($SiO_2$) divided by the molar amount of alumina ($Al_2O_3$) of 25.

Comparative Example 2: Comparative Catalyst for Upgrading Pyrolysis Oil

For Comparative Example 2, a comparative catalyst comprising a first catalyst metal and second catalyst metal deposited on the outer surfaces and pore surfaces of a nano-beta zeolite support was prepared using conventional metal precursors and no heteropolyacids. The first metal catalyst precursor was ammonium molybdate tetrahydrate having chemical formula $[(NH_3)_6Mo_7O_{24}.4H_2O]$, which was obtained from Sigma-Aldrich. The second metal catalyst precursor was cobalt (II) nitrate hexahydrate having chemical formula $[Co(NO_3)_2.6H_2O]$, which was also obtained from Sigma-Aldrich. The nano-beta zeolite catalyst support was the nano-beta zeolite catalyst support of Comparative Example 1.

The comparative catalyst of Comparative Example 2 was produced by adding 10 grams of the nano-beta zeolite catalyst support from Comparative Example 1 to a round bottom flask. A Solution A was prepared by dissolving 3.08 grams of $[(NH_3)_6Mo_7O_{24}.4H_2O]$ in 50 milliliters (mL) of distilled water. A Solution B was then prepared by dissolving 2.65 grams of the second metal catalyst precursor $[Co(NO_3)_2.6H_2O]$ in 50 mL of distilled water. The amounts of $[(NH_3)_6Mo_7O_{24}.4H_2O]$ and $[Co(N_3)_2.6H_2O]$ were selected to provide a final metal loading in the comparative catalyst of Comparative Example 2 of 3 wt. % Co and 12 wt. % Mo, respectively. Solution A and Solution B were then mixed together and added to nano-beta zeolite catalyst support in the round bottom flask. The combined solution and the nano-beta zeolite catalyst support were mixed for 2 hours. The water was removed from the nano-beta zeolite catalyst support impregnated with the first and second metal catalyst precursors under vacuum at a temperature of 50° C., and the solid sample was dried overnight at a temperature of 100° C. The solid sample was then calcined at a temperature of 500° C. for five hours to obtain the comparative catalyst of Comparative Example 2.

Comparative Example 3: Comparative Phosphorous-Containing Catalyst for Upgrading Pyrolysis Oil For Comparative Example 3, a comparative phosphorous-containing catalyst comprising a first catalyst metal, second catalyst metal, and phosphorous deposited on the outer surfaces and pore surfaces of a nano-beta zeolite support was prepared using conventional metal precursors and no heteropolyacids. The first metal catalyst precursor was ammonium molybdate tetrahydrate having chemical formula $[(NH_3)_6Mo_7O_{24}.4H_2O]$, which was obtained from Sigma-Aldrich. The second metal catalyst precursor was cobalt (II) nitrate hexahydrate having chemical formula $[Co(NO_3)_2.6H_2O]$, which was also obtained from Sigma-Aldrich. The nano-beta zeolite catalyst support was the nano-beta zeolite catalyst support of Comparative Example 1. Phosphoric acid ($H_3PO_4$) obtained from Sigma-Aldrich was used to incorporate the phosphorous.

The comparative phosphorous-containing catalyst of Comparative Example 3 was produced by adding 10 grams of the nano-beta zeolite catalyst support from Comparative Example 1 to a round bottom flask. A Solution A was prepared by dissolving 3.08 grams of the first metal catalyst precursor [$(NH_3)_6Mo_7O_{24} \cdot 4H_2O$] in 50 milliliters (mL) of distilled water. A Solution B was then prepared by dissolving 2.65 grams of the second metal catalyst precursor [$Co(N_3)_2 \cdot 6H_2O$] in 50 mL of distilled water. The amounts of [$(NH_3)_6Mo_7O_{24} \cdot 4H_2O$] and [$Co(NO_3)_2 \cdot 6H_2O$] were selected to provide a final metal loading in the comparative catalyst of Comparative Example 3 of 3 wt. % Co and 12 wt. % Mo, respectively. Solution A and Solution B were then mixed together, and 0.15 grams of phosphoric acid was dissolved in the combined solution to produce Solution C. Solution C was then added to the nano-beta zeolite catalyst support in the round bottom flask and mixed for 2 hours. The water was removed from the nano-beta zeolite catalyst support impregnated with the first and second metal catalyst precursors under vacuum at a temperature of 50° C., and the solid sample was dried overnight at a temperature of 100° C. The solid sample was then calcined at a temperature of 500° C. for five hours to obtain the comparative phosphorous-containing catalyst of Comparative Example 3.

Example 4: Multifunctional Catalyst for Upgrading Pyrolysis Oil Prepared Using a Heteropolyacid In Example 4, a multifunctional catalyst according to the present disclosure and comprising a first metal catalyst, a second metal catalyst, and phosphorous deposited on the outer surfaces and pore surfaces of a nano-beta zeolite support was prepared using a heteropolyacid for first metal catalyst precursor. The first metal catalyst precursor was phosphormolybdic heteropolyacid having chemical formula [$H_3PMo_{12}O_{40}$], which was obtained from Sigma-Aldrich. The second metal catalyst precursor was cobalt (II) nitrate hexahydrate having chemical formula [$Co(NO_3)_2 \cdot 6H_2O$], which was also obtained from Sigma-Aldrich. The nano-beta zeolite catalyst support was the nano-beta zeolite catalyst support of Comparative Example 1.

The multifunctional catalyst of Example 4 was produced by adding 10 grams of the nano-beta zeolite catalyst support from Comparative Example 1 to a round bottom flask. Solution A was prepared by dissolving 2.89 grams of the heteropolyacid of the first metal catalyst precursor [$H_3PMo_{12}O_{40}$] in 50 milliliters (mL) of distilled water. Solution B was then prepared by dissolving 2.24 grams of the second metal catalyst precursor [$Co(NO_3)_2 \cdot 6H_2O$] in 50 mL of distilled water. The amounts of the first metal catalyst precursor and second metal catalyst precursor were calculated to provide the same metal loading as the comparative catalysts of Comparative Examples 2 and 3 (3 wt. % Co and 12 wt. % Mo) Solution A and Solution B were then mixed together and added to the nano-beta zeolite catalyst support in the round bottom flask. The combined solution and nano-beta zeolite catalyst support were mixed for 2 hours. The water was removed from the nano-beta zeolite catalyst support impregnated with the first and second metal catalyst precursors under vacuum at a temperature of 50° C., and the solid sample was dried overnight at a temperature of 100° C. The solid sample was then calcined at a temperature of 500° C. for five hours to obtain the multifunctional catalyst of Example 4.

Example 5: Upgrading Pyrolysis Oil

In Example 5, the comparative catalysts of Comparative Examples 1, 2, and 3 and the multifunctional catalyst of Example 4 were used to upgrade a model pyrolysis oil composition to produce at least benzene, toluene, ethylbenzene, and xylene. 1-methylnaphthalene obtained from Sigma-Aldrich was used as the model pyrolysis oil.

Referring to FIG. 3, the apparatus 100 in which the model pyrolysis oil upgrading was conducted is schematically depicted. The apparatus 100 included a fixed bed reactor 110 with the catalyst loaded in zone 111. The fixed bed reactor 110 was maintained in a hot box 112 to maintain the fixed bed reactor 110 at constant temperature. The liquid feed 116, which included the model pyrolysis oil (1-methylnaphthalene) was introduced to the fixed bed reactor 110 using a liquid pump 120. Hydrogen 118 and nitrogen 119 can also be added to the liquid feed 116 upstream of the fixed bed reactor 110. The liquid feed 116 was passed through a heat exchanger 130 to adjust a temperature of the liquid feed 116 before passing it to the fixed bed reactor 110. The liquid feed 116 was contacted with the catalyst in the fixed bed reactor 110, the contacting causing reaction of at least the model pyrolysis oil (1-methylnaphthalene) to upgrade the model pyrolysis oil to produce a liquid product stream 114 comprising at least benzene, toluene, ethylbenzene, and xylene. The operating conditions of the fixed bed reactor 110 are listed in Table 1.

The liquid product stream 114 was passed from the fixed bed reactor 110 to a liquid gas separator 140, in which the liquid product stream 114 was separated into a gaseous fraction 142 comprising the lesser boiling temperature constituents and a liquid fraction 144 comprising the greater boiling point fractions and unreacted model pyrolysis oil (1-methylnaphthalene). The liquid fraction 144 was analyzed for composition. The gaseous fraction 142 was passed to an online gas chromatograph for analysis of the composition of the gaseous fraction 142. The compositions of the gaseous fraction 142 and liquid fraction 144 were then used to determine the yield for each of the constituents of the liquid product stream 114. The yields for each of the compounds produced in the fixed bed reactor for each of the catalysts of Comparative Examples 1-3 and Example 4 are provided subsequently in Table 1. The yields for each of the constituents in Table 1 are provided in weight percent based on the total mass flow rate of the liquid product stream 114.

TABLE 1

Results of Upgrading of Model Pyrolysis Oil with Catalysts of Comparative Examples 1-3 and Example 4

| | Comparative Example 1 | Comparative Example 2 | Comparative Example 3 | Example 4 |
|---|---|---|---|---|
| Catalyst Support | Nano-beta zeolite | Nano-beta zeolite | Nano-beta zeolite | Nano-beta zeolite |
| First Metal Catalyst Precursor | N/A | $(NH_3)_6Mo_7O_{24} \cdot 4H_2O$ | $(NH_3)_6Mo_7O_{24} \cdot 4H_2O$ | $H_3PMo_{12}O_{40}$ |
| Second Metal Catalyst Precursor | N/A | $Co(NO_3)_2 \cdot 6H_2O$ | $Co(NO_3)_2 \cdot 6H_2O$ | $Co(NO_3)_2 \cdot 6H_2O$ |

TABLE 1-continued

Results of Upgrading of Model Pyrolysis Oil with Catalysts of Comparative Examples 1-3 and Example 4

|  | Comparative Example 1 | Comparative Example 2 | Comparative Example 3 | Example 4 |
|---|---|---|---|---|
| Phosphorous Precursor | N/A | N/A | $H_3PO_4$ | $H_3PMo_{12}O_{40}$ |
| Catalyst Acidity ($\mu mol(NH_3)/g$) | 10788.0 | 4703.6 | 14570.0 | 3258.8 |
| Catalyst BET Surface Area ($m^2/g$) | 502.485 | 329.104 | 320.730 | 350.632 |
| Reaction Temperature (° C.) | 400 | 400 | 400 | 400 |
| Weight Hourly Space Velocity ($hour^{-1}$) | 1.2 | 1.2 | 1.2 | 1.2 |
| Total Pressure (MPa) | 3 | 3 | 3 | 3 |
| Total Conversion of 1-methylnaphthalene (%) | 32.3 | 86.1 | 81.8 | 86.7 |
| Time on Stream (hour) | 20 | 20 | 20 | 20 |
| Benzene Yield (wt. %) | 0.14 | 4.60 | 4.36 | 6.25 |
| Toluene Yield (wt. %) | 0.58 | 12.96 | 11.75 | 17.64 |
| Ethylbenzene Yield (wt. %) | 0.06 | 2.47 | 2.22 | 3.71 |
| Total Xylene Yield (wt. %) | 0.14 | 7.30 | 5.68 | 9.27 |
| Para-Xylene Yield (wt. %) | 0.03 | 1.78 | 1.40 | 2.28 |
| Meta-Xylene Yield (wt. %) | 0.07 | 3.83 | 2.99 | 4.86 |
| Ortho-Xylene Yield (wt. %) | 0.04 | 1.69 | 1.29 | 2.13 |
| C(3-4)-Benzene* Yield (wt. %) | 1.68 | 15.02 | 9.09 | 14.44 |
| Tetralin Yield (wt. %) | 0.04 | 0.60 | 0.23 | 0.34 |
| Naphthalene Yield (wt. %) | 0.98 | 2.53 | 2.31 | 2.92 |
| Methyltetralin Yield (wt. %) | 24.25 | 12.91 | 23.61 | 19.71 |
| Other 2-Ar (wt. %) | 6.18 | 8.89 | 7.32 | 7.36 |
| Total BTEX Yield** (wt. %) | 0.90 | 27.3 | 24.0 | 36.7 |

*C(3-4)-Benzene refers to benzene substituted with one or more alkyl group for which the total number of carbon atoms in the alkyl group is 3 or 4.
**Total BTEX Yield refers to the total combined yield of benzene, toluene, ethylbenzene, and xylenes (para-xylene, meta-xylene, and ortho-xylene).

As shown in Table 1, the multifunctional catalyst of Example 4 provided the best performance for upgrading the model pyrolysis oil (1-methylnaphthalene) to benzene, toluene, ethylbenzene, and xylenes (BTEX). The total BTEX yield obtained using the multifunctional catalyst of Example 4 was 36.7 wt. %, which is an improvement of greater than 34% over the comparative catalyst of Comparative Example 2. The multifunctional catalyst of Example 4 also resulted in the greatest overall conversion of 1-methylnaphthalene. Thus, at the same temperature and pressure, the multifunctional catalyst of the present application provides greater yield of BTEX compounds at lower pressures compared to conventional catalysts used to upgrade pyrolysis oils. Even though the multifunctional catalyst of Example 4 contained phosphorous, the multifunctional catalyst of Example 4 still exhibited a catalyst acidity less than the comparative catalyst of Comparative Example 2, which did not include phosphorous. Thus, the reduced acidity provided by the structure of the heteropolyacid used as the first metal catalyst precursor in the multifunctional catalyst of Example 4 may increase the yield of BTEX, compared to the comparative catalysts of Comparative Examples 2 and 3.

In a first aspect of the present disclosure, a method of making a multifunctional catalyst for upgrading pyrolysis oil may comprise contacting a zeolite support with a solution comprising at least a first metal catalyst precursor and a second metal catalyst precursor. The first metal catalyst precursor, the second metal catalyst precursor, or both, may comprise a heteropolyacid. The contacting may deposit the first metal catalyst precursor and the second catalyst precursor onto outer surfaces and pore surfaces of the zeolite support to produce a multifunctional catalyst precursor. The method may further include removing excess solution from the multifunctional catalyst precursor and calcining the multifunctional catalyst precursor to produce the multifunctional catalyst comprising at least a first metal catalyst and a second metal catalyst deposited on the outer surfaces and pore surfaces of the zeolite support.

In a second aspect of the present disclosure, a multifunctional catalyst for upgrading pyrolysis oil may comprise a multifunctional catalyst produced by a process comprising contacting a zeolite support with a solution comprising at least a first metal catalyst precursor and a second metal catalyst precursor, the first metal catalyst precursor, the second metal catalyst precursor, or both, comprising a heteropolyacid. The contacting may cause the first metal catalyst precursor and the second catalyst precursor to deposit onto outer surfaces and pore surfaces of the zeolite support to produce a multifunctional catalyst precursor. The process may further include removing excess solution from the multifunctional catalyst precursor and calcining the multifunctional catalyst precursor to produce the multifunctional catalyst. The multifunctional catalyst made by the process may include at least a first metal catalyst and a second metal catalyst deposited on the outer surfaces and the pore surfaces of the zeolite support.

A third aspect of the present disclosure may include either of the first or second aspects, in which the heteropolyacid comprises at least one metal selected from cobalt, molybdenum, vanadium, or combinations of these and at least one heteroatom selected from phosphorous, silicon, arsenic, or combinations of these.

A fourth aspect of the present disclosure may include any of the first through third aspects, in which the first metal catalyst precursor comprises a heteropolyacid.

A fifth aspect of the present disclosure may include any of the first through fourth aspects, in which the first metal catalyst precursor comprises a first heteropolyacid and the second metal catalyst precursor comprises a second heteropolyacid that is different from the first heteropolyacid.

A sixth aspect of the present disclosure may include any of the first through fifth aspects, in which the heteropolyacid comprises phosphormolybdic heteropolyacid having formula $H_3PMo_{12}O_{40}$.

A seventh aspect of the present disclosure may include any of the first through fifth aspects, in which the first metal catalyst precursor and the second metal catalyst precursor are the same heteropolyacid, and the heteropolyacid comprises a first metal, a second metal that is different from the first metal, and at least one heteroatom.

An eighth aspect of the present disclosure may include the seventh aspect, in which the heteropolyacid comprises decamolybdodicobaltate heteropolyacid.

A ninth aspect of the present disclosure may include any of the first through eighth aspects, further comprising dehydrating the heteropolyacid prior to contacting the zeolite support with the solution.

A tenth aspect of the present disclosure may include any of the first through ninth aspects, in which the multifunctional catalyst precursor is calcined at a temperature of 500-600° C. and for a time of from 4 hours to 6 hours to produce the multifunctional catalyst.

An eleventh aspect of the present disclosure may include any of the first through tenth aspects, in which the zeolite support comprises a nano beta zeolite having an average pore size of less than or equal to 2 micrometers.

A twelfth aspect of the present disclosure may include any of the first through eleventh aspects, in which the zeolite support comprises a molar ratio of silica to alumina of from 10 to 70.

A thirteenth aspect of the present disclosure may be the multifunctional catalyst produced according to any of the first through twelfth aspects.

A fourteenth aspect of the present disclosure may include any of the first through thirteenth aspects, in which the first metal catalyst comprises molybdenum and the second metal catalyst comprises cobalt.

A fifteenth aspect of the present disclosure may include any of the first through fourteenth aspects, further comprising phosphorous deposited on the outer surfaces and pore surfaces of the zeolite support.

A sixteenth aspect of the present disclosure may include any of the first through fifteenth aspects, in which the multifunctional catalyst has an acidity of less than 10,000 micromoles of ammonia per gram ($\mu mol(NH_3)/g$).

A seventeenth aspect of the present disclosure may include any of the first through sixteenth aspects, in which the multifunctional catalyst has an acidity of from 1000 $\mu mol(NH_3)/g$ to 5000 $\mu mol(NH_3)/g$.

An eighteenth aspect of the present disclosure may include any of the first through seventeenth aspects, in which the multifunction catalyst has a BET surface area of less than or equal to 400 meters squared per gram ($m^2/g$).

A nineteenth aspect of the present disclosure may include any of the first through eighteenth aspects, in which the multifunction catalyst has a BET surface area of from 200 $m^2/g$ to 400 $m^2/g$.

In a twentieth aspect of the present disclosure, a multifunctional catalyst for upgrading pyrolysis oil comprises one or more cobalt compounds, one or more molybdenum compounds, and phosphorous supported on a zeolite support, where at least one of the molybdenum compounds, cobalt compounds, or phosphorous is provided by a heteropolyacid precursor.

A twenty-first aspect of the present disclosure may include the twentieth aspect, in which the multifunctional catalyst has an acidity of less than 10,000 micromoles of ammonia per gram ($\mu mol(NH_3)/g$).

A twenty-second aspect of the present disclosure may include either of the twentieth or twenty-first aspects, in which the multifunctional catalyst has an acidity of from 1000 $\mu mol(NH_3)/g$ to 5000 $\mu mol(NH_3)/g$.

A twenty-third aspect of the present disclosure may include any of the twentieth through twenty-second aspects, in which the multifunction catalyst has a BET surface area of less than or equal to 400 meters squared per gram ($m^2/g$).

A twenty-fourth aspect of the present disclosure may include any of the twentieth through twenty-third aspects, in which the multifunction catalyst has a BET surface area of from 200 $m^2/g$ to 400 $m^2/g$.

A twenty-fifth aspect of the present disclosure may include any of the twentieth through twenty-fourth aspects, in which the heteropolyacid comprises phosphormolybdic heteropolyacid having formula $H_3PMo_{12}O_{40}$.

A twenty-sixth aspect of the present disclosure may include any of the twentieth through twenty-fifth aspects, in which the heteropolyacid comprises decamolybdodicobaltate heteropolyacid.

A twenty-seventh aspect of the present disclosure may include any of the twentieth through twenty-sixth aspects, in which the zeolite support comprises a nano beta zeolite having an average pore size of less than or equal to 2 micrometers.

A twenty-eighth aspect of the present disclosure may include any of the twentieth through twenty-seventh aspects, in which the zeolite support comprises a molar ratio of silica to alumina of from 10 to 70.

In a twenty-ninth aspect of the present disclosure, a method for upgrading pyrolysis oil includes contacting the pyrolysis oil with a multifunctional catalyst at mild reaction conditions comprising reaction temperatures of less than 500 degrees Celsius (° C.) and pressures less than 6 megapascals (MPa). The pyrolysis oil may include multi-ring aromatic compounds. The multifunctional catalyst may be produced by a process comprising contacting a zeolite support with a solution comprising at least a first metal catalyst precursor and a second metal catalyst precursor, the first metal catalyst precursor, the second metal catalyst precursor, or both, comprising a heteropolyacid. The contacting may cause the first metal catalyst precursor and the second catalyst precursor to deposit onto outer surfaces and pore surfaces of the zeolite support to produce a multifunctional catalyst precursor. The process for producing the multifunctional catalyst may further include removing excess solution from the multifunctional catalyst precursor and calcining the multifunctional catalyst precursor to produce the multifunctional catalyst. The multifunctional catalyst comprises at least a first metal catalyst and a second metal catalyst supported on the zeolite support. Contact of the pyrolysis oil with the multifunctional catalyst at the reaction conditions converts at least a portion of the multi-ring aromatic compounds in the pyrolysis oil to one or more C6-C8 aromatic compounds.

A thirtieth aspect of the present disclosure may include the twenty-ninth aspect, in which the C6-C8 aromatic compounds include one or more of benzene, toluene, ethylbenzene, xylene, or combinations of these.

A thirty-first aspect of the present disclosure may include the twenty-ninth or thirtieth aspects, in which contacting the pyrolysis oil with the multifunctional catalyst at the reaction conditions converts the portion of the multi-ring aromatic compounds in the pyrolysis oil to C6-C8 aromatic compounds in a single step, without conducting a subsequent chemical reaction step.

A thirty-third aspect of the present disclosure may include any of the twenty-ninth through thirty-first aspects, where contacting the pyrolysis oil with the multifunctional catalyst results a yield of C6-C8 aromatic compounds of at least 30%.

A thirty-fourth aspect of the present disclosure may include any of the twenty-ninth through thirty-third aspects, further comprising separating an upgraded pyrolysis oil from the multifunctional catalyst.

A thirty-fifth aspect of the present disclosure may include any of the twenty-ninth through thirty-fourth aspects, in which the pyrolysis oil is contacted with the multifunctional catalyst at a temperature of from 300° C. to 450° C.

A thirty-sixth aspect of the present disclosure may include any of the twenty-ninth through thirty-fifth aspects, in which the pyrolysis oil is contacted with the multifunctional catalyst at a pressure of from 0.1 MPa to 5 MPa.

A thirty-seventh aspect of the present disclosure may include any of the twenty-ninth through thirty-sixth aspects, in which the heteropolyacid comprises at least one metal selected from cobalt, molybdenum, vanadium, or combinations of these and at least one heteroatom selected from phosphorous, silicon, arsenic, or combinations of these.

A thirty-eighth aspect of the present disclosure may include any of the twenty-ninth through thirty-seventh aspects, in which the first metal catalyst precursor comprises a heteropolyacid.

A thirty-ninth aspect of the present disclosure may include any of the twenty-ninth through thirty-eighth aspects, in which the first metal catalyst precursor comprises a first heteropolyacid and the second metal catalyst precursor comprises a second heteropolyacid that is different from the first heteropolyacid.

A fortieth aspect of the present disclosure may include any of the twenty-ninth through thirty-ninth aspects, in which the heteropolyacid comprises phosphormolybdic heteropolyacid having formula $H_3PMo_{12}O_{40}$.

A forty-first aspect of the present disclosure may include any of the twenty-ninth through thirty-ninth aspects, in which the first metal catalyst precursor and the second metal catalyst precursor are the same heteropolyacid, and the heteropolyacid comprises a first metal, a second metal that is different from the first metal, and at least one heteroatom.

A forty-second aspect of the present disclosure may include the forty-first aspect, in which the heteropolyacid comprises decamolybdodicobaltate heteropolyacid.

A forty-third aspect of the present disclosure may include any of the twenty-ninth through forty-second aspects, further comprising dehydrating the heteropolyacid prior to contacting the zeolite support with the solution.

A forty-fourth aspect of the present disclosure may include any of the first through forty-third aspects, in which the multifunctional catalyst precursor is calcined at a temperature of 500-600° C. and for a time of from 4 hour to 6 hours to produce the multifunctional catalyst.

A forty-fifth aspect of the present disclosure may include any of the twenty-ninth through forty-fourth aspects, in which the zeolite support comprises a nano beta zeolite having an average pore size of less than or equal to 2 micrometers.

A forty-sixth aspect of the present disclosure may include any of the twenty-ninth through forty-fifth aspects, in which the zeolite support comprises a molar ratio of silica to alumina of from 10 to 70.

A forty-seventh aspect of the present disclosure may include any of the twenty-ninth through forty-sixth aspects, in which the first metal catalyst comprises molybdenum and the second metal catalyst comprises cobalt.

A forty-eighth aspect of the present disclosure may include any of the twenty-ninth through forty-seventh aspects, further comprising phosphorous deposited on the outer surfaces and pore surfaces of the zeolite support.

A forty-ninth aspect of the present disclosure may include any of the twenty-first through forty-eighth aspects, in which the multifunctional catalyst has an acidity of less than 10,000 micromoles of ammonia per gram ($\mu mol(NH_3)/g$).

A fiftieth aspect of the present disclosure may include any of the twenty-ninth through forty-ninth aspects, in which the multifunctional catalyst has an acidity of from 1000 $\mu mol$ $(NH_3)/g$ to 5000 $\mu mol(NH_3)/g$.

A fifty-first aspect of the present disclosure may include any of the twenty-ninth through fiftieth aspects, in which the multifunction catalyst has a BET surface area of less than or equal to 400 meters squared per gram ($m^2/g$).

A fifty-second aspect of the present disclosure may include any of the twenty-ninth through fifty-first aspects, in which the multifunction catalyst has a BET surface area of from 200 $m^2/g$ to 400 $m^2/g$.

It should now be understood that various aspects of the multifunctional catalyst for upgrading pyrolysis oil, methods of making the multifunctional catalyst for upgrading pyrolysis oil using heteropolyacids as the metal catalyst precursors, and methods of upgrading pyrolysis oils using the methods are described and such aspects may be utilized in conjunction with various other aspects.

Throughout this disclosure, ranges are provided for various properties and characteristics of the multifunctional catalyst and various processing parameters and operating conditions for the methods for making the multifunctional catalyst and upgrading pyrolysis oil. It will be appreciated that when one or more explicit ranges are provided the individual values and the sub-ranges formed within the range are also intended to be provided as providing an explicit listing of all possible combinations is prohibitive. For example, a provided range of 1-10 also includes the individual values, such as 1, 2, 3, 4.2, and 6.8, as well as all the ranges, which may be formed within the provided bounds, such as 1-8, 2-4, 6-9, and 1.3-5.6.

It should be apparent to those skilled in the art that various modifications and variations can be made to the described embodiments without departing from the spirit and scope of the claimed subject matter. Thus, it is intended that the specification cover the modifications and variations of the various described embodiments provided such modifications and variations come within the scope of the appended claims and their equivalents.

What is claimed is:

1. A multifunctional catalyst produced by a method of making a multifunctional catalyst for upgrading pyrolysis oil, the method comprising:
   contacting a zeolite support with a solution comprising at least a first metal catalyst precursor and a second metal catalyst precursor, the first metal catalyst precursor, the second metal catalyst precursor, or both, comprising a heteropolyacid and the zeolite support comprising a molar ratio of silica to alumina of from 10 to 70, where the contacting deposits the first metal catalyst precursor and the second metal catalyst precursor onto outer surfaces and pore surfaces of the zeolite support to produce a multifunctional catalyst precursor;
   removing excess solution from the multifunctional catalyst precursor; and
   calcining the multifunctional catalyst precursor at a temperature of at least 500 degrees Celsius to produce the multifunctional catalyst comprising at least a first metal catalyst and a second metal catalyst deposited on the outer surfaces and pore surfaces of the zeolite support, and
   where the multifunctional catalyst has an acidity of less than 10,000 micromoles of ammonia per gram ($\mu$mol $(NH_3)$/g).

2. The multifunctional catalyst of claim 1, in which the first metal catalyst comprises molybdenum and the second metal catalyst comprises cobalt.

3. The multifunctional catalyst of either of claim 1, further comprising phosphorous deposited on the outer surfaces and pore surfaces of the zeolite support.

4. The multifunctional catalyst of claim 1, in which the multifunction catalyst has a BET surface area of less than or equal to 400 meters squared per gram ($m^2$/g).

5. The multifunctional catalyst of claim 1, in which the heteropolyacid comprises phosphormolybdic heteropolyacid having formula $H_3PMo_{12}O_{40}$.

6. The multifunctional catalyst of claim 1, in which the heteropolyacid comprises decamolybdodicobaltate heteropolyacid.

7. The multifunctional catalyst of claim 1, in which the zeolite support comprises a nano beta zeolite having an average pore size of less than or equal to 2 micrometers.

8. The multifunctional catalyst of claim 1, in which the solution includes from 1 weight percent (wt. %) to 20 wt. % of the first metal catalyst precursor.

9. The multifunctional catalyst of claim 1, in which the solution includes from 1 wt. % to 20 wt. % of the second metal catalyst precursor.

10. The multifunctional catalyst of claim 1, in which the solution does not include an organic compound.

11. The multifunctional catalyst of claim 1, in which the first metal of the first metal precursor consists of molybdenum.

12. The multifunctional catalyst of claim 1, in which the second metal of the second metal precursor consists of cobalt.

13. The multifunctional catalyst of claim 1, in which the multifunctional catalyst has an acidity of from 1000 $\mu$mol $(NH_3)$/g to 5000 $\mu$mol$(NH_3)$/g.

14. The multifunctional catalyst of claim 1, in which the multifunctional catalyst does not include a binder or a matrix.

15. The multifunctional catalyst of claim 1, in which the heteropolyacid comprises at least one heteroatom selected from the group consisting of phosphorous, silicon, germanium, arsenic, and combinations of these.

* * * * *

UNITED STATES PATENT AND TRADEMARK OFFICE
CERTIFICATE OF CORRECTION

PATENT NO. : 11,027,271 B2  
APPLICATION NO. : 16/916234  
DATED : June 8, 2021  
INVENTOR(S) : Miao Sun Page 1 of 1

It is certified that error appears in the above-identified patent and that said Letters Patent is hereby corrected as shown below:

In the Specification

In Column 8, Line(s) 7, delete "$H_{io}[SiV_6Mo_6O_{40}]$" and insert --$H_{10}[SiV_6Mo_6O_{40}]$--, therefor.

In Column 14, Line(s) 29, delete "$[Co(N_3)_26H_2O]$" and insert --$[Co(NO_3)_26H_2O]$--, therefor.

In Column 15, Line(s) 3 & 4, delete "$[Co(N_3)_26H_2O]$" and insert --$[Co(NO_3)_26H_2O]$--, therefor.

Signed and Sealed this  
Fourth Day of January, 2022

Drew Hirshfeld  
*Performing the Functions and Duties of the*  
*Under Secretary of Commerce for Intellectual Property and*  
*Director of the United States Patent and Trademark Office*